(12) United States Patent
Arayama et al.

(10) Patent No.: US 9,078,791 B2
(45) Date of Patent: Jul. 14, 2015

(54) DISPOSABLE WORN ARTICLE

(75) Inventors: Takaya Arayama, Kagawa (JP);
Hirotomo Mukai, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 231 days.

(21) Appl. No.: 13/580,533

(22) PCT Filed: Feb. 23, 2011

(86) PCT No.: PCT/JP2011/053939
§ 371 (c)(1),
(2), (4) Date: Oct. 12, 2012

(87) PCT Pub. No.: WO2011/105412
PCT Pub. Date: Sep. 1, 2011

(65) Prior Publication Data
US 2013/0030402 A1      Jan. 31, 2013

(30) Foreign Application Priority Data

Feb. 27, 2010 (JP) ................................. 2010-043595

(51) Int. Cl.
*A61F 13/494* (2006.01)
*A61F 13/496* (2006.01)
*A61F 13/49* (2006.01)

(52) U.S. Cl.
CPC ......... *A61F 13/496* (2013.01); *A61F 13/49019* (2013.01); *A61F 13/49406* (2013.01)

(58) Field of Classification Search
CPC .................... A61F 13/49019; A61F 13/49017; A61F 2013/455
See application file for complete search history.

(56) References Cited

U.S. PATENT DOCUMENTS

| | | | | |
|---|---|---|---|---|
| 5,197,959 A | * | 3/1993 | Buell | 604/385.23 |
| 5,662,634 A | | 9/1997 | Yamamoto et al. | |
| 6,056,732 A | * | 5/2000 | Fujioka et al. | 604/385.01 |
| 6,198,019 B1 | * | 3/2001 | Hansson et al. | 604/378 |
| 6,423,042 B1 | * | 7/2002 | Sasaki | 604/385.01 |
| 8,361,047 B2 | | 1/2013 | Mukai et al. | |

(Continued)

FOREIGN PATENT DOCUMENTS

| | | |
|---|---|---|
| EP | 1723939 A1 | 11/2006 |
| JP | 621463 | 6/1994 |

(Continued)

OTHER PUBLICATIONS

Extended European Search Report dated May 19, 2014, corresponds to European patent application No. 11747372.8.

(Continued)

*Primary Examiner* — Susan Su
(74) *Attorney, Agent, or Firm* — Lowe Hauptman & Ham, LLP

(57) ABSTRACT

A disposable worn article diaper includes: a central slit formed in an absorber such that the absorber is curved to be convex toward an inward direction toward a wearer in a crotch region; side curved portions formed in the absorber along the lengthwise direction such that the absorber is curved to be convex toward the outward direction. The disposable worn article diaper includes a crossing elastic member crossing the absorber in middle crotch regions and fixed to the absorber. The absorber is contracted by the crossing elastic member toward a center of the absorber in the widthwise direction.

14 Claims, 12 Drawing Sheets

(56) References Cited

U.S. PATENT DOCUMENTS

| | | | |
|---|---|---|---|
| 2002/0068919 A1* | 6/2002 | Shinohara et al. | 604/385.27 |
| 2002/0147439 A1* | 10/2002 | Tanaka et al. | 604/398 |
| 2006/0264859 A1 | 11/2006 | Tsuji et al. | |
| 2008/0140042 A1 | 6/2008 | Mukai et al. | |
| 2010/0324521 A1 | 12/2010 | Mukai et al. | |
| 2010/0324523 A1 | 12/2010 | Mukai et al. | |
| 2012/0289923 A1* | 11/2012 | Watabe et al. | 604/385.201 |

FOREIGN PATENT DOCUMENTS

| | | | |
|---|---|---|---|
| JP | 2001190592 A | | 7/2001 |
| JP | 200362009 A | | 3/2003 |
| JP | 2004065524 | | 3/2004 |
| JP | 2006122396 | | 5/2006 |
| JP | 2006346439 | | 12/2006 |
| JP | 2006346439 A | | 12/2006 |
| JP | 2010279612 A | | 12/2010 |
| JP | 2011177308 A | | 9/2011 |
| JP | 2011177310 A | | 9/2011 |
| WO | 2008069279 | | 6/2008 |
| WO | 2009069343 A1 | | 6/2009 |

OTHER PUBLICATIONS

International Search Report and Written Opinion for PCT/JP2011/053939 mailed May 24, 2011.

Office Action mailed Sep. 3, 2013 corresponds to Japanese patent application No. 2010-043595.

Office Action mailed Sep. 29, 2014, corresponding to Chinese patent application No. 201180011204.X.

Office Action issued Feb. 17, 2015, corresponding to Australian patent application No. 2011221332.

\* cited by examiner

DISPOSABLE WORN ARTICLE

RELATED APPLICATIONS

The present application is a national phase of PCT/JP2011/053939, filed Feb. 23, 2011 and is based on, and claims priority from, Japanese Application Number 2010-043595, filed Feb. 27, 2010.

TECHNICAL FIELD

The present invention relates to a disposable worn article having an absorber at which a curved portion to curve the absorber is formed.

BACKGROUND ART

In a disposable worn article such as a pant-type diaper, in order to serve to improve the comfort of a wearer at the time of the wearing and to prevent leakage of bodily waste, various means have been devised.

For example, there has been known a pant-type diaper in which three curved portions are formed at an absorber for absorbing the bodily waste of the wearer along the lengthwise direction of the absorber (for example, Patent Literature 1).

Specifically, in the pant-type diaper, the absorber is formed with three slits, and a peripheral portion of each slit is curved at the time of wearing of the pant-type diaper.

A peripheral portion of a central slit is convex toward the excretion portion of the wearer.

Furthermore, a peripheral portion of a side slits is convex in opposition to the peripheral portion of the central slit.

That is, the sectional shape of the absorber along the widthwise direction of the absorber is modified to a W-letter shape.

Therefore, the convex portion of the absorber formed by the peripheral portion of the central slit is easy to make close contact with the excretion portion of the wearer.

Furthermore, the bodily waste is easy to enter into concave portions formed by the peripheral portion of two outer side slits, so that it is possible to prevent the skin of the wearer from making direct contact with the bodily waste.

Furthermore, in the pant-type diaper, a pair of constricted portions are formed around the boundary between the crotch region and the waistline region, wherein the constricted portions are constricted toward the center in the widthwise direction of the absorber by cutting out a part of the absorber, so that the W-letter shaped sectional shape does not affect a waistline region positioned back and forth of a crotch region.

CITATION LIST

Patent Literature

[PTL 1] Japanese Unexamined Patent Application Publication No. 2006-346439 (Page 9, FIG. 8)

SUMMARY OF INVENTION

However, in the aforementioned conventional pant-type diaper, the constricted portions are formed by cutting out the absorber, resulting in a reduction in the capacity of the absorber.

Therefore, no special problems occur in mild incontinence. However, when it is necessary to increase an absorption amount, since it is difficult to increase an absorption area in the periphery of the constricted portions, it is not possible to easily increase the absorption amount.

Particularly, when the wearer is in a lying posture, leakage becomes more significant from the middle crotch region at the back of the wearer positioned behind the crotch region. That is, for the wearer in the lying posture for a long time, if it is possible to increase absorbing power in the middle crotch region at the back of the wearer positioned behind the crotch region, it will significantly contribute to preventing the leakage of the bodily waste for moderate or more incontinence.

Therefore, the present invention has been achieved in view of the above-described problems, and an object thereof is to provide a disposable worn article, such as a pant-type diaper, capable of reliably serving to improve the comfort of a wearer when wearing the disposable worn article and prevent the leakage of bodily waste by curving an absorber, and further improving absorbing power.

The present invention is summarized as a disposable worn article (for example, a pant-type diaper 1) including: a front waistline region (a front waistline region S2); a back waistline region (a back waistline region S3); a crotch region (a crotch region S1) positioned between the front waistline region and the back waistline region, and brought into contact with a crotch portion of a wearer; a pair of middle crotch regions (a foreside middle crotch region S4, and a backside middle crotch region S5) positioned between the crotch region and the front waistline region and between the crotch region and the back waistline region; an absorber (an absorber 40) having a lengthwise direction (a lengthwise direction L), a widthwise direction (a widthwise direction W) perpendicular to the lengthwise direction, an inward direction (an inward direction IN) toward the wearer, and an outward direction (an outward direction OUT) toward the opposite to the inward direction; a central curved portion (a central slit 45) formed in the absorber along the lengthwise direction such that the absorber is curved to be convex toward the inward direction in the crotch region; a pair of side curved portions (side slits 46L, 46R) formed in the absorber along the lengthwise direction such that the absorber is curved to be convex toward the outward direction at outside of the widthwise direction from the central curved portion; and a crossing elastic member (a crossing elastic member 7A) crossing the absorber along the widthwise direction in at least either of the pair of middle crotch regions, and fixed to the absorber, wherein an apex surface (apex surface 45a) of the absorber being convex by the central curved portion toward the inward direction is configured to make contact with the crotch portion, and the absorber is contracted by the crossing elastic member toward a center of the absorber in the widthwise direction.

According to the characteristics of the present invention, it is possible to provide a disposable worn article, such as a pant-type diaper, capable of further improving absorbing power in the case of serving to improve the comfort of a wearer when wearing the disposable worn article and to prevent the leakage of bodily waste by curving an absorber.

DESCRIPTION OF EMBODIMENTS

Figure 1:
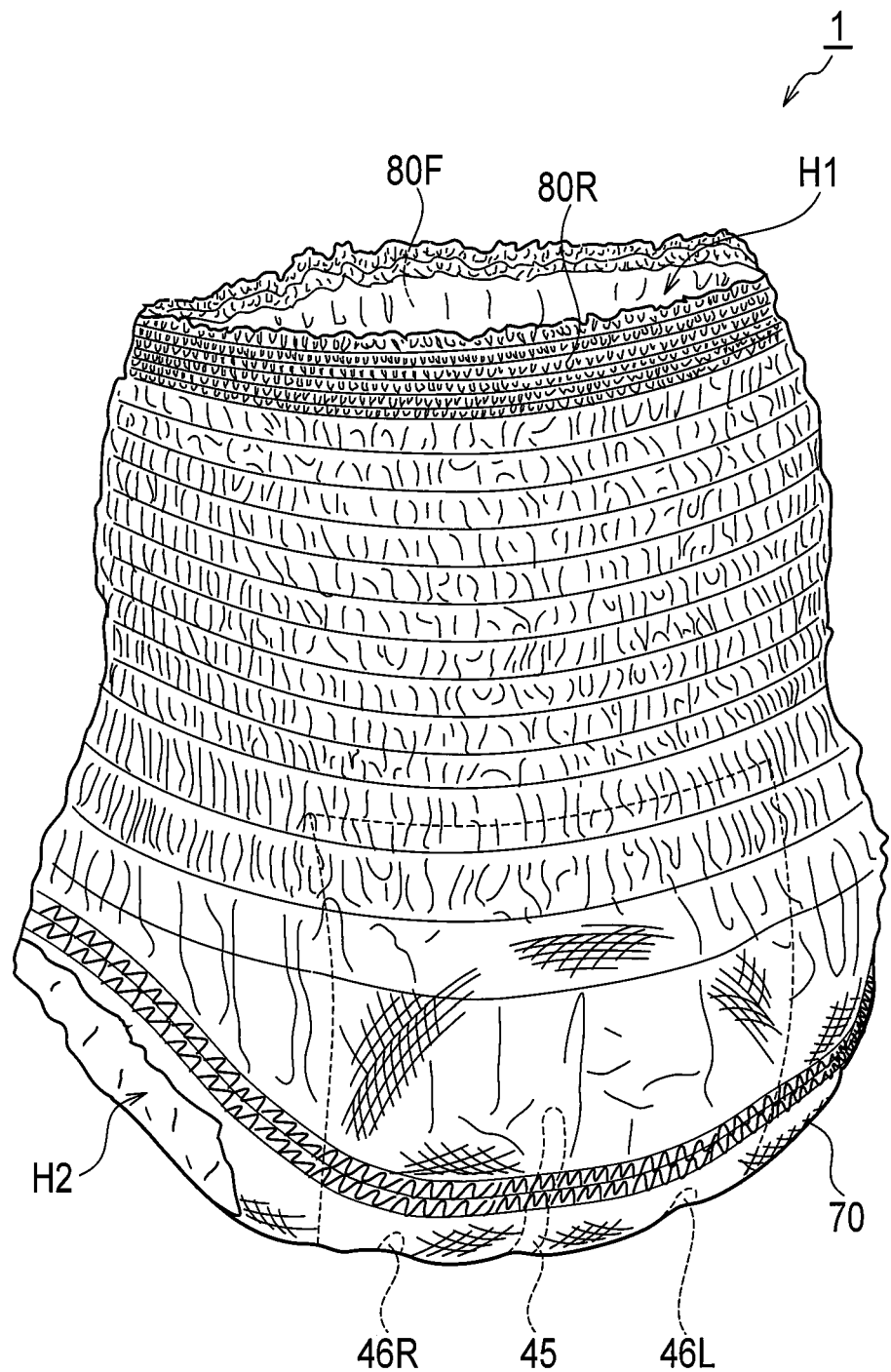
FIG. 1 is a schematic perspective view of a disposable diaper 1 according to a first embodiment.

Next, embodiments of a disposable worn article according to the present invention will be described with reference to the drawings.

Specifically, a first embodiment, a second embodiment, a third embodiment, and other embodiments will be described.

In the following description of the drawings, the same or similar reference numerals are used to designate the same or similar parts.

It will be appreciated that the drawings are schematically shown and the ratio and the like of each dimension are different from the real ones.

Accordingly, specific dimensions should be determined in consideration of the explanation below.

Moreover, among the drawings, the respective dimensional relations or ratios may differ.

[First Embodiment]

A disposable worn article according to the present embodiment is provided with a crossing elastic member which crosses an absorber along the widthwise direction of the absorber in a middle crotch region and is fixed to the absorber. The absorber is characterized in that the absorber is contracted by the crossing elastic member toward the center in the widthwise direction of the absorber.

(1) Entire Schematic Configuration of Disposable Worn Article

FIG. 1 is a schematic perspective view of a disposable diaper 1 that configures the disposable worn article in the present embodiment.

As illustrated in FIG. 1, the disposable diaper 1 is a pant-type disposable diaper formed with a waistline opening H1 and a pair of leg-hole openings H2.

The disposable diaper 1 includes an exterior topsheet 70 and a foreside exterior backsheet 80F, which configure an exterior portion of the disposable diaper 1, and a backside exterior backsheet 80R.

At an inner side (a skin contact surface side) of the exterior topsheet 70, an absorber 40 configured from cotton-like pulp and highly polymerized water absorbent polymer is provided.

The absorber 40 is formed with a plurality of slits.

Specifically, a central slit 45 is formed in the center in the widthwise direction of the absorber 40.

Furthermore, a side slit 46L and a side slit 46R are formed at both sides of the central slit 45.

By these slits formed in the absorber 40, the absorber 40 is configured to be curved at the time of wearing of the disposable diaper 1.

Figure 2:
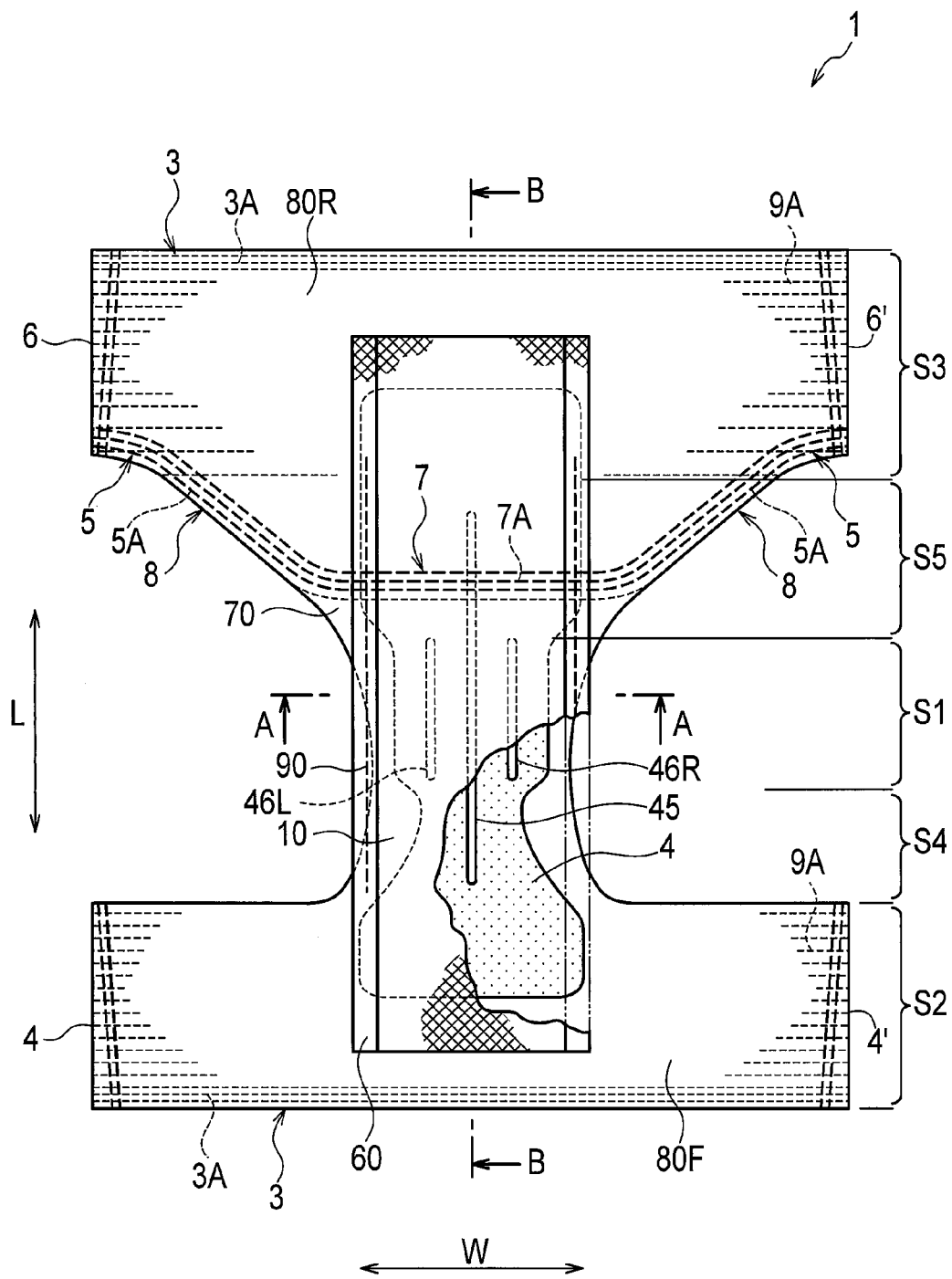
FIG. 2 is an exploded plan view of the disposable diaper 1 according to the first embodiment.

FIG. 2 is an exploded plan view of the disposable diaper 1 according to the present embodiment.

Figure 3:
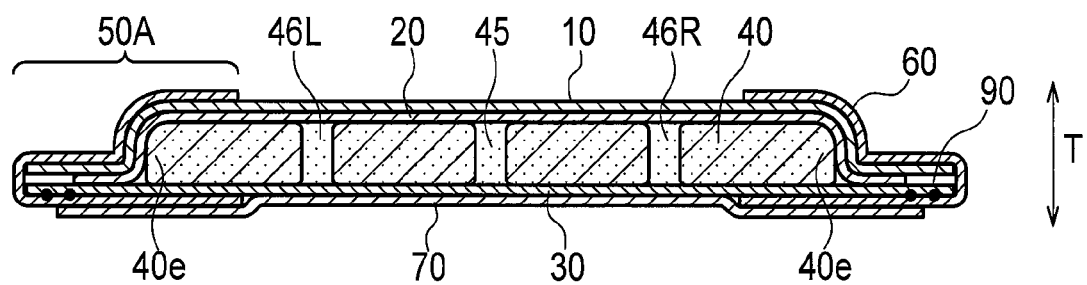
FIG. 3 is a widthwise sectional view of the disposable diaper 1 along a line A-A illustrated in FIG. 2.

FIG. 3 is a widthwise sectional view of the disposable diaper 1 along a line A-A illustrated in FIG. 2.

Figure 4:
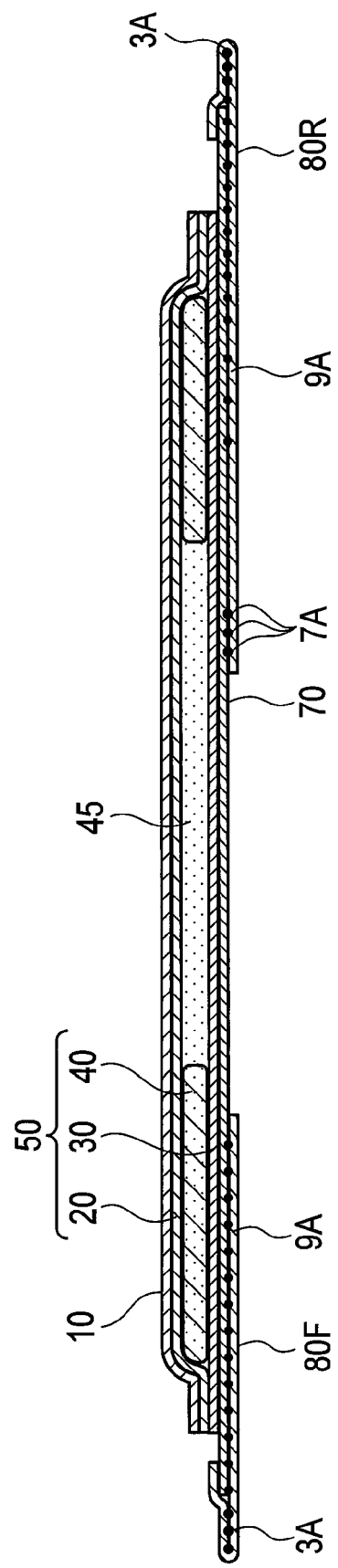
FIG. 4 is a lengthwise sectional view of the disposable diaper 1 along a line B-B illustrated in FIG. 2.

FIG. 4 is a lengthwise sectional view of the disposable diaper 1 along a line B-B illustrated in FIG. 2.

As illustrated in FIG. 2 to FIG. 4, the disposable diaper 1 has a front waistline region S2 corresponding to a front waistline of a wearer, and a back waistline region S3 corresponding to a back waistline of the wearer.

Furthermore, the disposable diaper 1 has a crotch region S1, a foreside middle crotch region S4, and a backside middle crotch region S5.

The crotch region S1 is positioned between the front waistline region S2 and the back waistline region S3, and is a region brought into contact with a crotch portion of the wearer, in which the width between both legs is the narrowest when the wearer closes both legs.

The foreside middle crotch region S4 is positioned between the crotch region S1 and the front waistline region S2 in the lengthwise direction L of the absorber 40.

The backside middle crotch region S5 is positioned between the crotch region S1 and the back waistline region S3 in the lengthwise direction L.

A front waistline side edge portion 4 is joined with a back waistline edge portion 6, and a front waistline edge portion 4' is joined with a back waistline edge portion 6', so that the disposable diaper 1 is formed to have a pant shape.

The front waistline region S2 and the back waistline region S3 are provided with waist gathers 3.

The waist gathers 3 have an elongated waist elastic member 3A of synthetic rubber, for example, that is laid out to expand and contract along the widthwise direction W of the absorber 40.

The waist elastic member 3A is joined with the exterior topsheet 70, the foreside exterior backsheet 80F, and the backside exterior backsheet 80R by an adhesive (for example, a hot-melt adhesive) in the state in which the waist elastic member 3A has been expanded along the widthwise direction W of the disposable diaper 1.

At a middle crotch edge portion 8 of the backside exterior backsheet 80R, leg gathers 5 and absorber crossing gathers 7 are formed.

The leg gathers 5 are formed to run along the leg portions of the wearer.

The absorber crossing gathers 7 are formed to cross the absorber 40 along the widthwise direction W.

The leg gather 5 has a plurality of (three) leg elastic members 5A and the absorber crossing gather 7 has a plurality of (three) crossing elastic members 7A linked to the leg elastic members 5A.

The crossing elastic member 7A is integrally linked to the leg elastic member 5A and extends to the back waistline region S3.

The crossing elastic member 7A crosses the absorber 40 along the widthwise direction W and is fixed to the absorber 40 (specifically, an absorber body 50) in the backside middle crotch region S5.

Therefore, the absorber 40 is contracted by the crossing elastic member 7A toward the center of the absorber 40 in the widthwise direction W.

In addition, for convenience of explanation, FIG. 2 illustrates a state in which the absorber 40 is not contracted.

Furthermore, the foreside exterior backsheet 80F and the backside exterior backsheet 80R are provided with fit elastic bodies 9A extending along the widthwise direction W.

The disposable diaper 1 includes a topsheet 10, the absorber 40, sidesheets 60, the exterior topsheet 70, the foreside exterior backsheet 80F, and the backside exterior backsheet 80R.

The topsheet 10, the absorber 40, the sidesheets 60, the exterior topsheet 70, and the foreside exterior backsheets 80F and 80R are joined with one another by an adhesive, thermal fusion bonding or the like.

The topsheet 10 is a sheet that forms the skin contact surface that can be in direct contact with the skin of the wearer.

The topsheet 10 is formed by a liquid-permeable sheet, such as a hydrophilic nonwoven cloth and woven cloth, an aperture plastic film, or an aperture hydrophobic nonwoven cloth.

An absorber topside covering sheet 20 is provided between the topsheet 10 and the absorber 40 in the thickness direction T.

The absorber topside covering sheet 20 is formed by a liquid-permeable sheet, such as a hydrophilic nonwoven cloth and woven cloth, an aperture plastic film, an aperture hydrophobic nonwoven cloth, or a tissue.

An absorber backside covering sheet 30 is provided at the non-skin contact surface side, which is the surface opposite the topsheet 10 and the absorber topside covering sheet 20 via the absorber 40.

The absorber backside covering sheet 30 is formed by a leakage-preventing sheet of a liquid-impermeable film (for example, polyethylene) or the like.

In addition, although omitting to illustrate in FIG. 3, the absorber topside covering sheet 20 is joined with the absorber backside covering sheet 30 in positions in which the slits (the central slit 45 and the side slits 46L and 46R) are formed.

In addition, it may be possible to employ a configuration in which instead of the absorber topside covering sheet 20, the topsheet 10 is joined with the absorber backside covering sheet 30 in the positions in which the slits (the central slit 45 and the side slits 46L and 46R) are formed.

The absorber 40 is covered by the topsheet 10, the absorber topside covering sheet 20, and the absorber backside covering sheet 30.

The absorber 40 is covered by the topsheet 10, the absorber topside covering sheet 20, and the absorber backside covering sheet 30, so that the absorber body 50 is formed.

The absorber 40 has the lengthwise direction L toward the back waistline region S3 from the front waistline region S2, and the widthwise direction W perpendicular to the lengthwise direction L.

Additionally, the absorber 40 has an inner direction IN toward the wearer wearing the disposable diaper 1 and an outer direction OUT toward the opposite side of the inner direction.

As described above, the crossing elastic member 7A crosses the absorber 40 along the widthwise direction W and is fixed to the absorber 40 in the backside middle crotch region S5.

The crossing elastic member 7A is provided at the non-skin contact surface side of the absorber 40, specifically, between the exterior topsheet 70 and the backside exterior backsheet 80R.

That is, in the present embodiment, the fact that "the crossing elastic member 7A is fixed to the absorber 40" means that the crossing elastic member 7A is joined to the absorber 40 through the absorber backside covering sheet 30 and the exterior topsheet 70.

As the crossing elastic member 7A, for example, it is possible to use synthetic rubber, such as styrene butadiene, butadiene, isoprene, or neoprene, natural rubber, EVA, elastic polyolefin, spandex, foamed polyurethane, or the like.

In the present embodiment, as the crossing elastic member 7A, three spandexes of 780 dtex, the expansion magnification of which has increased to two times on an average, are used.

The absorber 40 is obtained by combining cotton-like pulp of 200 g/m2 with absorbent polymer of 200 g/m2.

Furthermore, the absorber 40 is formed with the central slit 45, the side slit 46L, and the side slit 46R as described above.

The central slit 45 is formed in the absorber 40 along the lengthwise direction L such that the absorber 40 can be curved to be convex in the inward direction IN, that is, to be convex toward the wearer.

In the present embodiment, the central slit 45 configures a central curved portion.

The side slit 46L and the side slit 46R are formed in the absorber 40 along the lengthwise direction L such that the absorber 40 can be curved to be convex in the outward direction OUT at outside of the widthwise direction W from the central slit 45, that is, to be convex to the opposite side of the central slit 45.

In the present embodiment, the side slit 46L and the side slit 46R configure side curved portions.

The central slit 45 has a width of about 10 mm and a length of about 200 mm.

The side slit 46L and the side slit 46R have a width of about 10 mm and a length of about 120 mm.

Furthermore, the absorber 40 has a thickness of about 2.0 mm.

In addition, it is preferable that the central slit 45, and the side slits 46L and 46R have a width of 5 mm to 12 mm.

At the outside of the widthwise direction W of the absorber 40, side elastic members 90 in a state of expanded along the lengthwise direction L are provided at side edges 50A at which the topsheet 10 and the absorber backside covering sheet 30 overlap each other.

The side elastic member 90 is provided outside side ends 40e of the absorber 40 along the lengthwise direction L, and continues from the foreside middle crotch region S4 to the backside middle crotch region S5 via the crotch region S1.

The side elastic member 90 is provided between the absorber backside covering sheet 30 and the sidesheets 60.

The side elastic member 90 is formed by synthetic rubber, for example, having elasticity.

The sidesheets 60 are provided on both ends of the widthwise direction W of the absorber 40 so as to wrap the topsheet 10, the absorber topside covering sheet 20, and the absorber backside covering sheet 30 as one part.

The sidesheets 60 are formed by sheets of liquid-impermeable nonwoven cloth, for example, and a leakage-preventing wall for preventing the side leakage of bodily waste is configured by the sidesheets 60 and the side elastic member 90.

The exterior topsheet 70 is formed from the front waistline region S2 to the back waistline region S3 via the foreside middle crotch region S4, the crotch region S1, and the backside middle crotch region S5.

The exterior topsheet 70 is formed to have a larger width of the widthwise direction W in the front waistline region S2 and the back waistline region S3, as compared with other areas.

The exterior topsheet 70 may be formed by an air-through nonwoven cloth, a spun bond nonwoven cloth, an SMS nonwoven cloth, a water-resistive film or the like.

The foreside exterior backsheet 80F is provided at more non-skin contact surface side than the exterior topsheet 70 in the front waistline region S2.

The backside exterior backsheet 80R is provided at more non-skin contact surface side than the exterior topsheet 70 in the back waistline region S3.

A one end of the foreside exterior backsheet 80F (the backside exterior backsheet 80R) in the lengthwise direction L is folded back to the skin contact surface side and is provided to wrap an end in the lengthwise direction L of the exterior topsheet 70.

The foreside exterior backsheet 80F can be formed by an air-through nonwoven cloth, a spun bond nonwoven cloth, an SMS nonwoven cloth, or a water-resistive film.

As for each member configuring the aforementioned disposable diaper 1, the material described in Japanese Unexamined Patent Publication No. 2006-346439, for example, may be used.

(2) Shape of Joining Portion of Absorber Body

Figure 5:
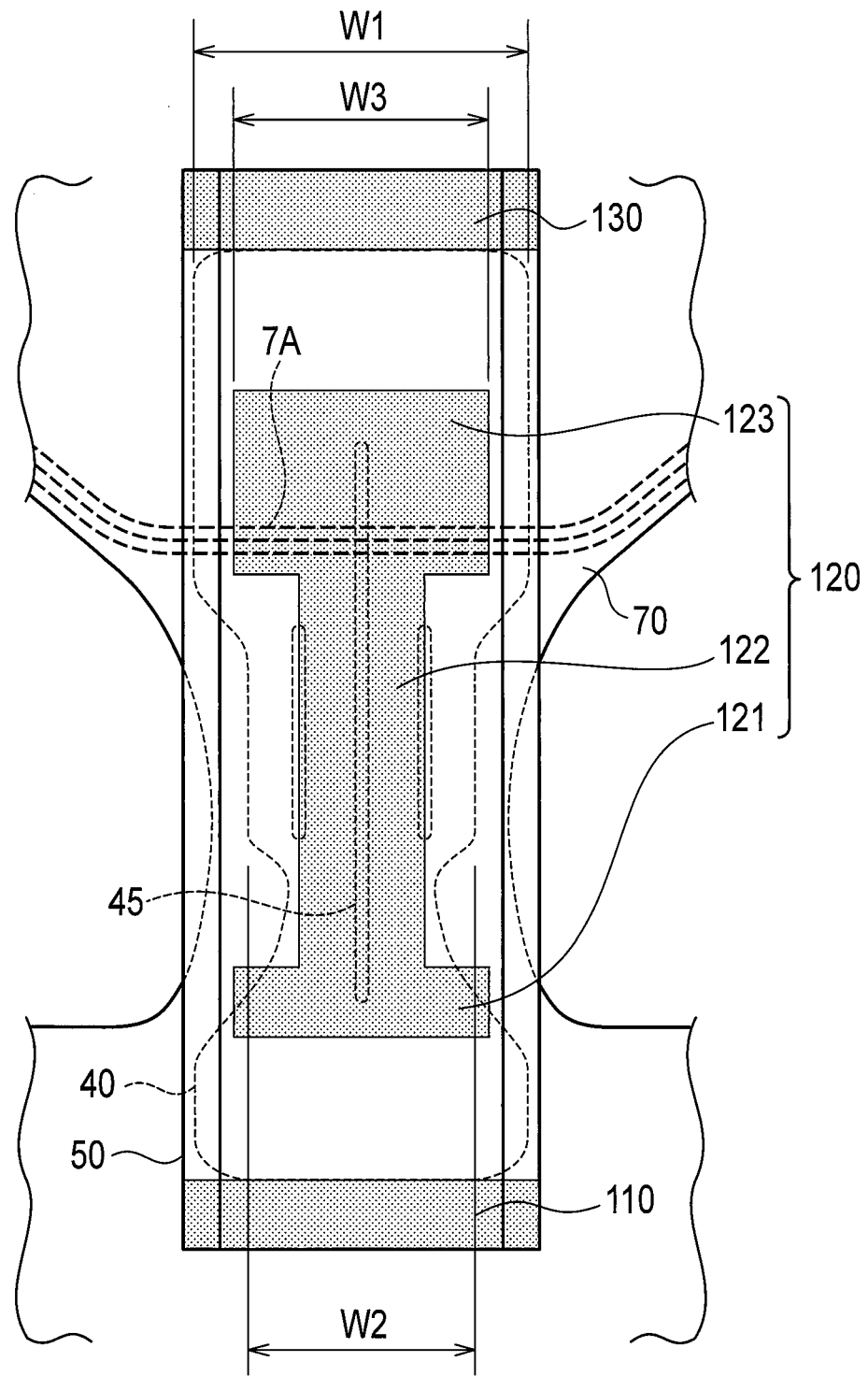
FIG. 5 is a plan view illustrating a joining portion between an absorber body 50 and an exterior topsheet 70 according to the first embodiment.

FIG. 5 is a plan view illustrating a joining portion between the absorber body 50 and the exterior topsheet 70.

As illustrated in FIG. 5, the absorber body 50 in which the absorber 40 is covered by the topsheet 10, the absorber topside covering sheet 20, and the absorber backside covering sheet 30 is joined with the exterior topsheet 70 in a plurality of places independently separated from one another.

Specifically, the absorber body 50 is joined with the exterior topsheet 70 by the adhesive (for example, the hot-melt adhesive) in a joining portion 110, a joining portion 120, and a joining portion 130.

The joining portion 110 is formed in the front waistline region S2, and the joining portion 130 is formed in the back waistline region S3 (refer to FIG. 2).

The joining portion 120 is formed over the crotch region S1, the foreside middle crotch region S4, and the backside middle crotch region S5.

The joining portion 120 includes a wide portion 121, a wide portion 123, and a narrow portion 122 formed between the wide portion 121 and the wide portion 123.

The joining portion 120 is formed in a wider range than the central slit 45.

It is preferable that a width W1 of the absorber 40 in the backside middle crotch region S5 is equal to or more than a width W2 of the crotch region S1.

Furthermore, it is preferable that a width W3 (a width of the wide portion 123) where the crossing elastic member 7A is joined with and fixed to the absorber 40 (the absorber body 50) is narrower than the width W1 of the absorber 40 in the backside middle crotch region S5.

In this case, at both ends of the absorber 40, portions not fixed to the crossing elastic member 7A is provided.

In addition, it is preferable that the width W3 corresponds to about 70% of the width W1.

Furthermore, in the present embodiment, among the central slit 45, the side slit 46L, and the side slit 46R, the crossing elastic member 7A crosses only the central slit 45.

(3) Changes in Shape of Absorber

Figure 6:
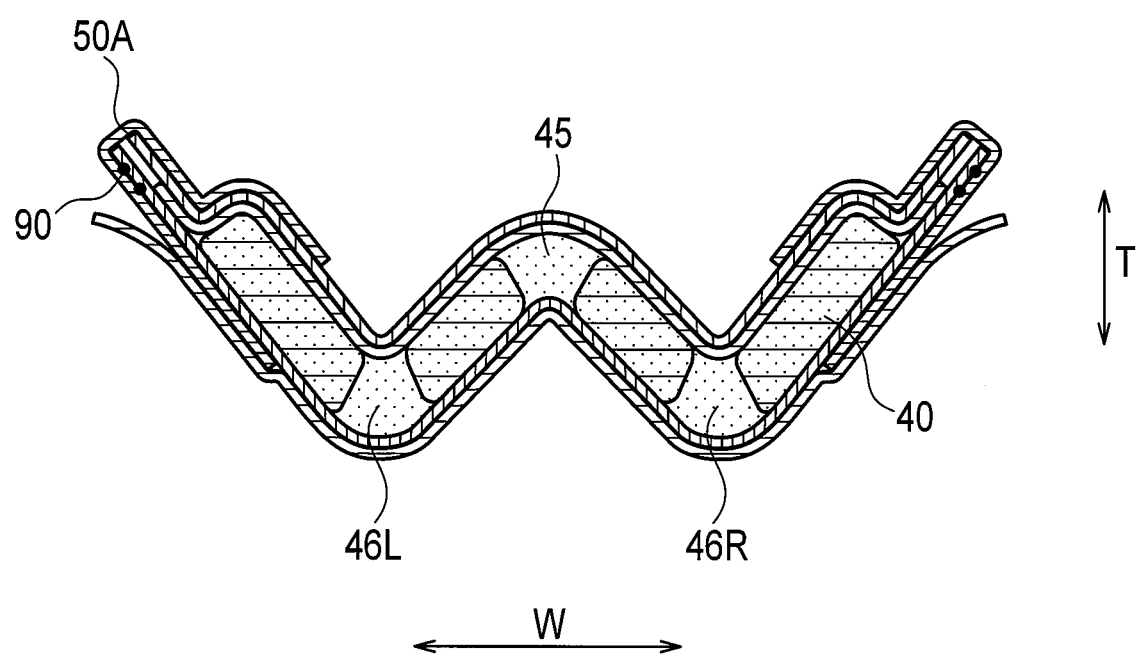
FIG. 6 is a sectional view schematically illustrating a wearing state of the disposable diaper 1 according to the first embodiment.

FIG. 6 is a sectional view schematically illustrating a wearing state of the disposable diaper 1 (the line A-A of FIG. 2 as the reference).

As illustrated in FIG. 6, if the disposable diaper 1 is worn, since the absorber 40 is curved about the central slit 45, the side slit 46L, and the side slit 46R, the sectional shape of the disposable diaper 1 along the widthwise direction W is modified to a W-letter shape.

As a consequence, an apex surface 45a (not illustrated in FIG. 6, refer to FIG. 8) of the absorber 40 being convex by the central slit 45 in the inward direction IN makes contact with the crotch portion of the wearer.

Figure 7:
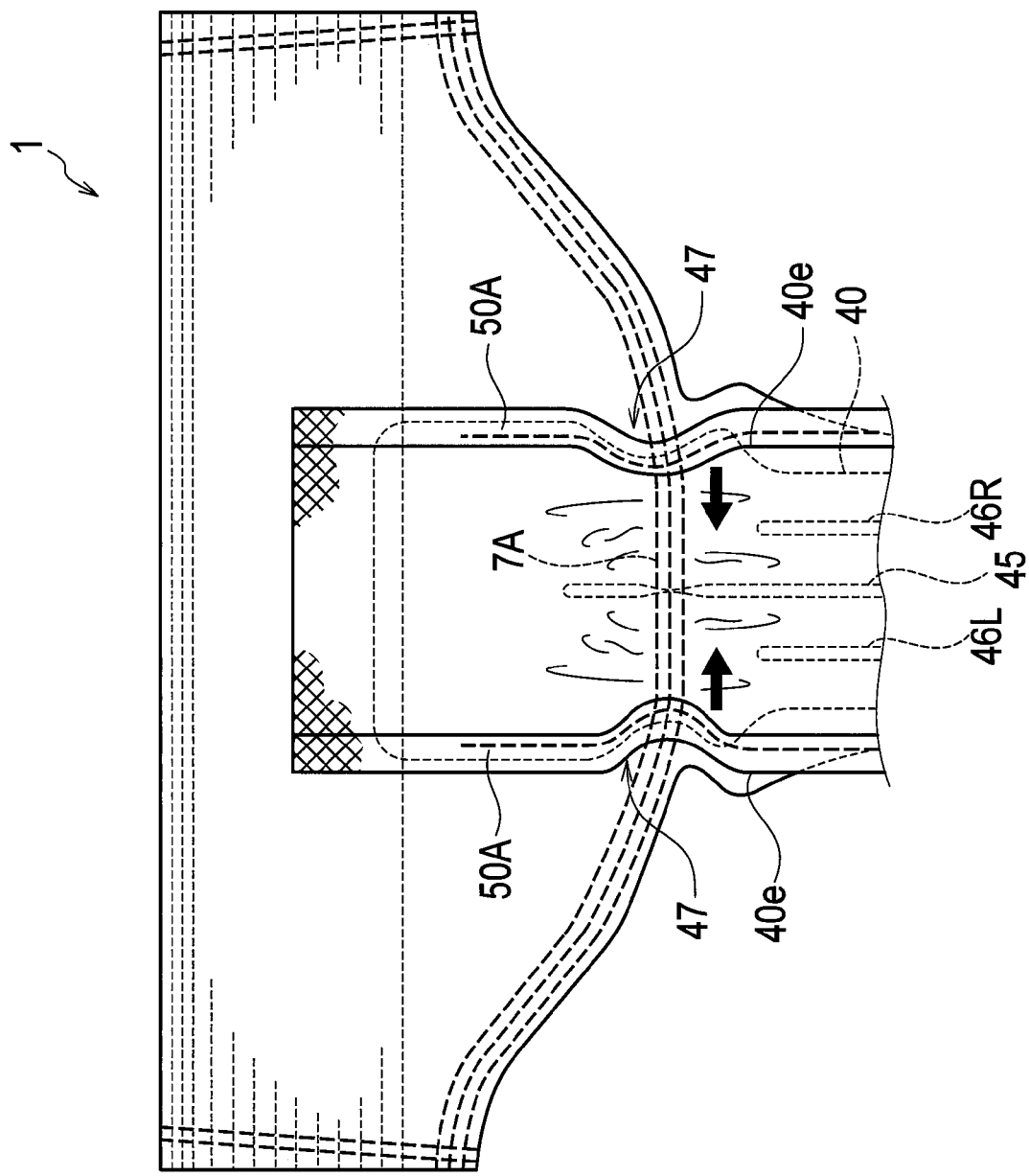
FIG. 7 is a partially exploded plan view of the disposable diaper 1 in which an absorber 40 has been contracted by a crossing elastic member 7A.

FIG. 7 is a partially exploded plan view of the disposable diaper 1 in which the absorber 40 is contracted by the crossing elastic member 7A.

Figure 8:
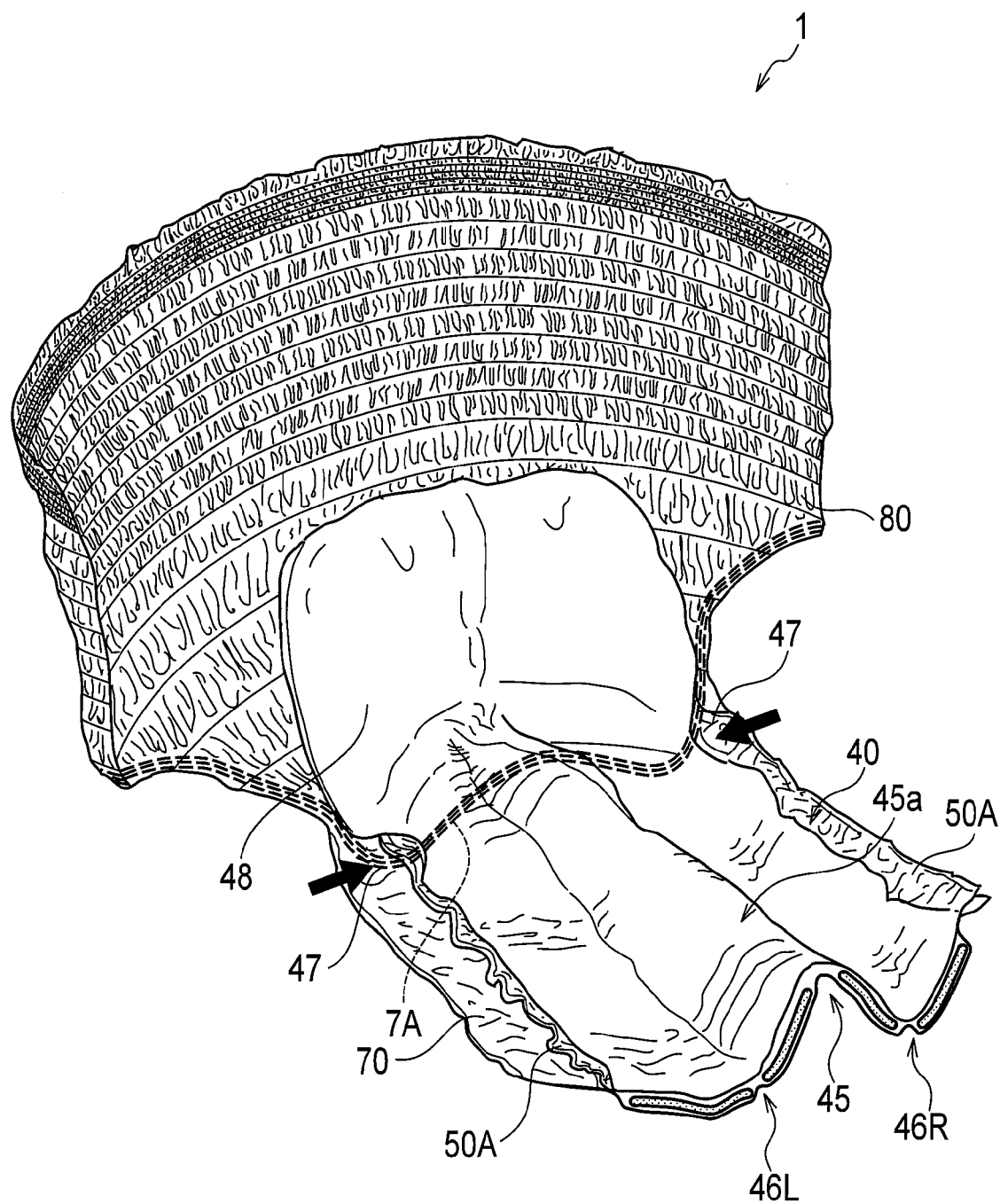
FIG. 8 is a partially enlarged perspective view illustrating a wearing state of the disposable diaper 1 according to the first embodiment.

FIG. 8 is a partially enlarged perspective view illustrating a wearing state of the disposable diaper 1 according to the first embodiment.

As illustrated in FIG. 7 and FIG. 8, the absorber 40 is contracted by the crossing elastic member 7A toward the center of the absorber 40 in the widthwise direction W (refer to arrows in figures).

Specifically, since the crossing elastic member 7A is provided to cross the absorber 40 along the widthwise direction W at an expansion magnification of two times on the average and is fixed to the absorber 40 (the absorber body 50), thereby allowing the absorber 40 to be contracted toward the center in the widthwise direction W.

When the width W3 (refer to FIG. 5) in which the crossing elastic member 7A is fixed to the absorber 40 is equal to the width W1 of the absorber 40 in the backside middle crotch region S5, the absorber 40 is contracted over the entire width, particularly, the side ends 40e of the absorber 40 are concaved, so that concave portions 47 are formed.

That is, the width of the absorber 40 in the backside middle crotch region S5 in the state in which the crossing elastic member 7A is contracted is narrower than the width of the absorber 40 in the backside middle crotch region S5 in the state in which the crossing elastic member 7A is expanded.

Specifically, in the present embodiment, the width of the absorber 40 in the backside middle crotch region S5 in the state in which the crossing elastic member 7A is been contracted is configured to be narrow by about 15 mm at one side, the total about 30 mm, as compared with the width W1 in the state in which the crossing elastic member 7A is expanded.

In addition, it is preferable that the concave portion 47 is formed up to an extension line of the side slit 46L (the side slit 46R) as viewed from a plan view of the absorber 40.

Meanwhile, when the width W3 is narrower than the width W1, only a portion at which the crossing elastic member 7A is fixed to the absorber 40, that is, a portion excluding the side ends 40e is contracted.

In this case, since the side ends 40e not fixed to the crossing elastic member 7A are easy to freely move, the side edges 50A (leg standing gathers) are easy to rise, as compared with the case in which the width W3 is equal to the width W1.

Furthermore, the side ends 40e not fixed to the crossing elastic member 7A are easy to rise upward together with the side edges 50A.

Therefore, the side ends 40e crossed by the crossing elastic member 7A rise, so that the concave portions 47 are formed.

In addition, the crossing elastic member 7A may not cross the entire width of the absorber 40, and it is sufficient if the concave portions 47 are formed.

Furthermore, as illustrated in FIG. 8, if the disposable diaper 1 is worn, the central slit 45 is modified to be convex toward the wearer (the inward direction IN) to form the apex surface 45a.

Meanwhile, the side slit 46L (the side slit 46R) is modified to be convex toward the non-skin contact surface side (the outward direction OUT).

Specifically, while the central slit 45 is interposed between both legs of the wearer to be convex toward the wearer, the side slit 46L (the side slit 46R) rises toward the wearer by the contraction of the side edge 50A.

Thus, the section along the widthwise direction W of the absorber 40 is modified to the W-letter shape, so that the apex surface 45a can make close contact with the crotch portion of the wearer without being separated therefrom.

Moreover, since the absorber 40 is contracted by the crossing elastic member 7A, the influence of the modification to the W-letter shape in the crotch region S1 is blocked at a portion of the crossing elastic member 7A, so that it is possible to prevent the modification to the W-letter shape from affecting a rear portion 48 of the absorber 40 positioned closer to the back side than the crossing elastic member 7A.

That is, since the rear portion 48 does not form the W-letter shape and maintains a flat shape also at the time of wearing, the surface of the absorber 40 makes close contact with the skin of the wearer at outside of the lengthwise direction L from the crotch region S1, so that it is possible to effectively prevent bodily waste such as urine from being leaked along the skin of the wearer.

Furthermore, in the conventional disposable diaper, in order to prevent the modification to the W-letter shape from affecting the rear portion 48, a constricted portion constricted by cutting out a part of the absorber 40 is formed in the backside middle crotch region S5.

However, in the disposable diaper 1, since the absorber 40 is only contracted, an actual effective absorption area (capacity) of the absorber 40 is not reduced.

Thus, it is possible to improve absorbing power of urine or the like.

Furthermore, the concave portions 47 formed when the absorber 40 is contracted by the crossing elastic member 7A can prevent the modification to the W-letter shape from affecting the rear portion 48, similarly to the constricted portion formed by cutting out a part of the absorber 40.

In addition, as described above, the concave portions 47 are formed up to the extension line of the side slit 46L (the side slit 46R), thereby effectively preventing the modification to the W-letter shape from affecting the rear portion 48.

That is, according to the disposable diaper 1, it is possible to reliably serve to improve the comfort of a wearer at the time of wearing and to prevent the leakage of bodily waste by curving the absorber 40, and to further improve absorbing power.

Particularly, the disposable diaper 1 is effective for moderate incontinence or more.

In the present embodiment, the crossing elastic member 7A is provided at the non-skin contact surface side of the absorber 40, specifically, between the exterior topsheet 70 and the backside exterior backsheet 80R.

Thus, even when the crossing elastic member 7A crosses the absorber 40 in the backside middle crotch region S5, it is difficult for the wearer to have an uncomfortable feeling.

Furthermore, since the crossing elastic member 7A is provided at the non-skin contact surface side of the absorber 40, even when the absorber 40 is modified to the W-letter shape, a part outside of the widthwise direction W from the side slit 46L (the side slit 46R) is further developed outward and the central slit 45 is easy to be convex.

In the present embodiment, the crossing elastic member 7A is provided in the backside middle crotch region S5.

Thus, the shape of the rear portion 48 of the absorber 40 positioned at back side from the crossing elastic member 7A can be flat, and particularly, the disposable diaper 1 is effective for a wearer in the lying posture for a long time.

In the present embodiment, among the central slit 45, and the side slits 46L and 46R, the crossing elastic member 7A crosses only the central slit 45.

Thus, if the absorber 40 is contracted by the crossing elastic member 7A, it is possible to reliably narrow the width of the absorber 40 corresponding to the width of the central slit 45.

In the present embodiment, the absorber topside covering sheet 20 is joined with the absorber backside covering sheet 30 in the positions in which the slits (the central slit 45, and the side slits 46L and 46R) are formed.

Thus, it is possible to prevent the slit portions from being closed after the absorber 40 is modified, and to prevent the absorber 40 from being distorted from the slit portions.

Furthermore, even when the absorber 40 absorbs liquid and is expanded, it is possible to prevent the slit portions from being closed, thereby making it easy for the slit portions to reliably function as curved portions.

[Second Embodiment]

Next, a configuration of a disposable diaper 1X according to a second embodiment will be described with reference to the drawing.

Note that the same reference numerals have been used for the same portions as the disposable diaper 1 according to the aforementioned first embodiment, and mainly, the differences have been explained.

Figure 9:
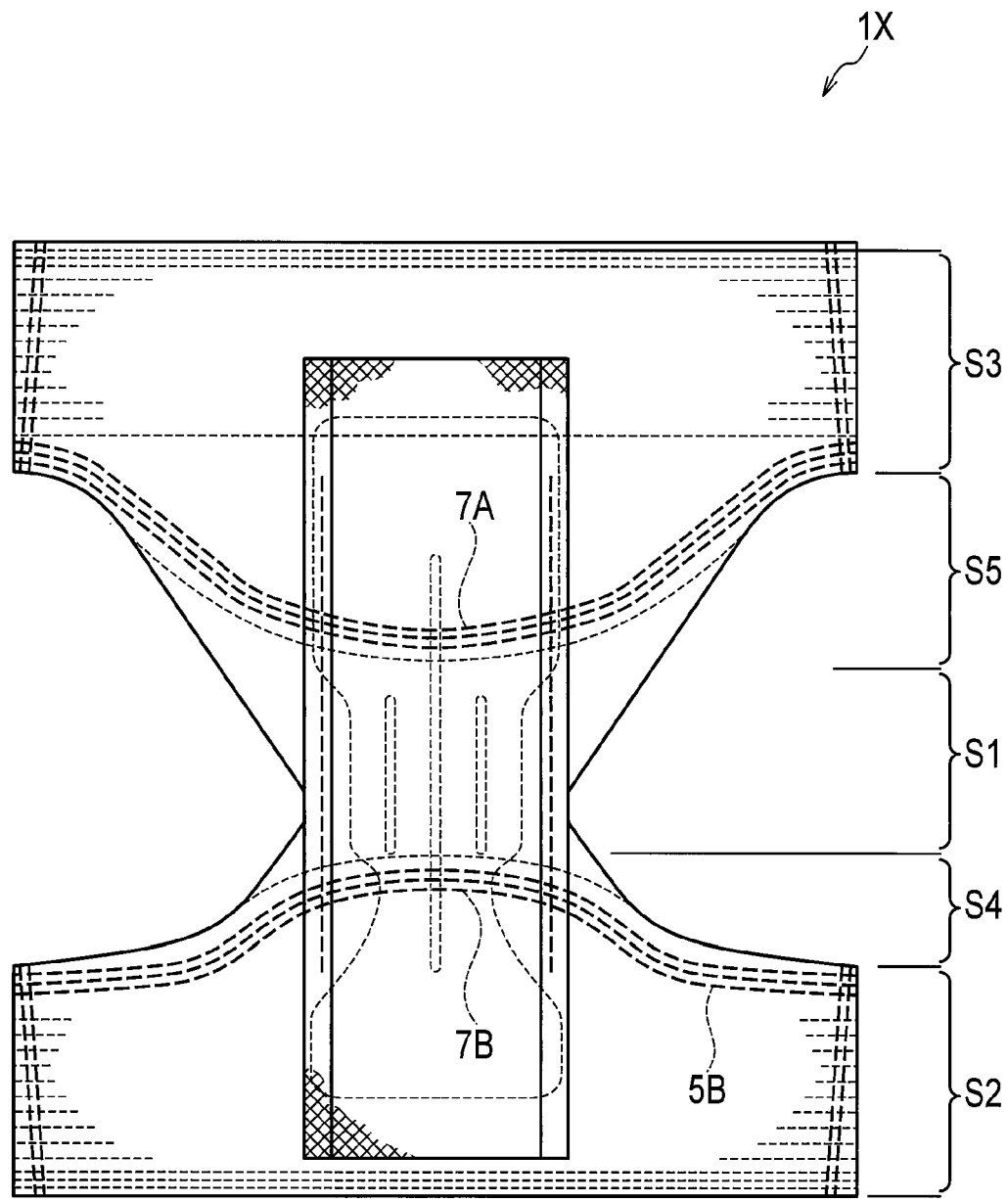
FIG. 9 is an exploded plan view of a disposable diaper 1X according to a second embodiment.

FIG. 9 is an exploded plan view of the disposable diaper 1X according to the second embodiment.

In the aforementioned disposable diaper 1 according to the first embodiment, the crossing elastic member 7A has been provided only in the backside middle crotch region S5.

On the other hand, in the disposable diaper 1X, in addition to the crossing elastic member 7A provided in the backside middle crotch region S5, a crossing elastic body 7B having a similar function to that of the crossing elastic member 7A is also provided in the foreside middle crotch region S4.

The crossing elastic body 7B is integrally linked to a leg elastic member 5B to contract the absorber 40 in the foreside middle crotch region S4.

That is, in the disposable diaper 1X, the absorber 40 is contracted in both the foreside middle crotch region S4 and the backside middle crotch region S5.

According to the disposable diaper 1X, since the absorber 40 is also contracted in the foreside middle crotch region S4, it is possible to prevent the modification to the W-letter shape from affecting the front waistline region S2 at the time of wearing of the disposable diaper 1X.

That is, the surface of the absorber 40 makes close contact with the skin of a wearer at outside of the lengthwise direction L from areas interposed between the crossing elastic member 7A and the crossing elastic body 7B, so that it is possible to effectively prevent bodily waste such as urine from being leaked along the skin of the wearer.

[Third Embodiment]

Next, a configuration of a disposable diaper 1Y according to a third embodiment will be described with reference to the drawing.

Note that the same reference numerals have been used for the same portions as the disposable diaper 1 according to the aforementioned first embodiment, and mainly, the differences have been explained.

Figure 10:
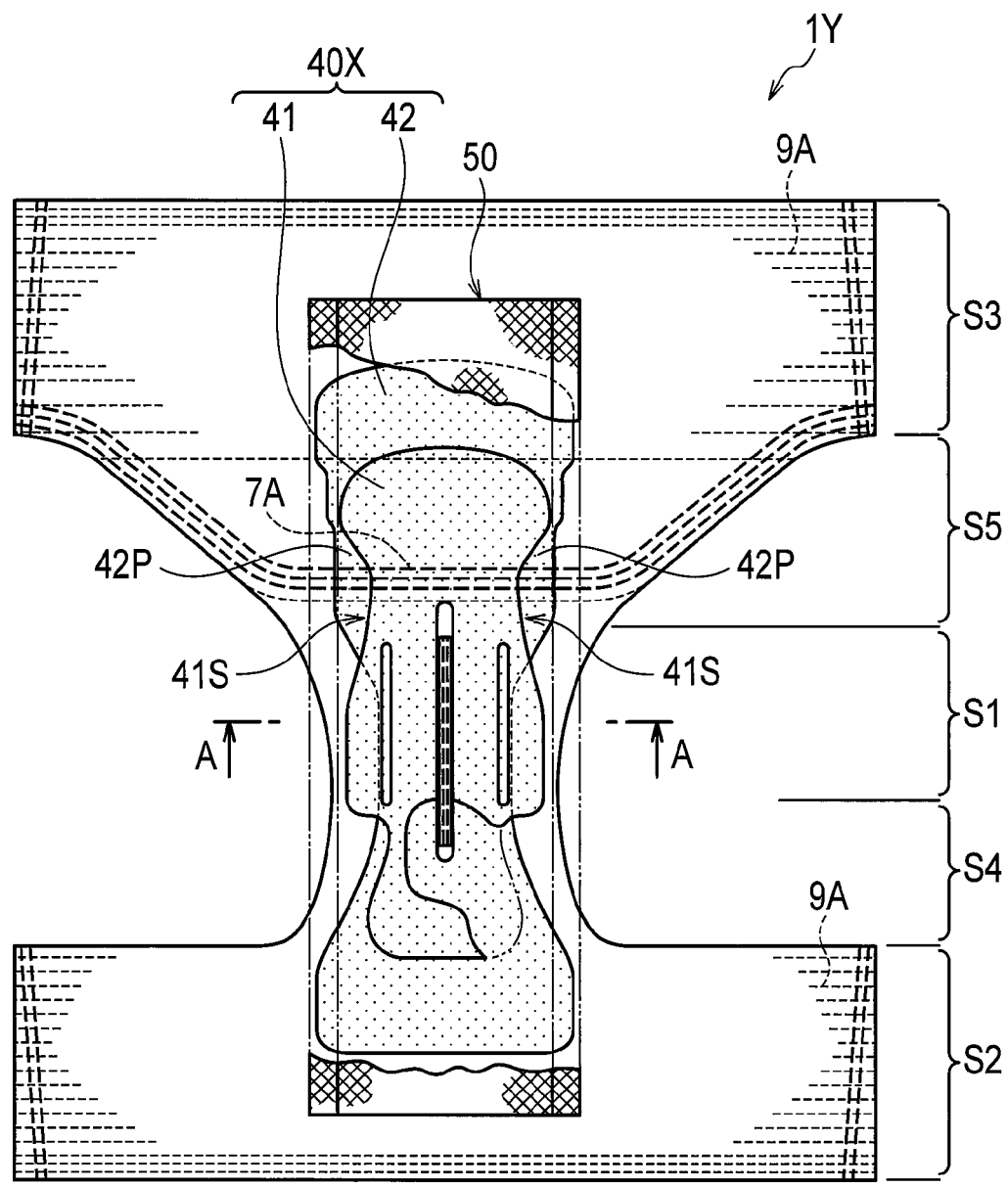
FIG. 10 is an exploded plan view of a disposable diaper 1Y according to a third embodiment.

FIG. 10 is an exploded plan view of the disposable diaper 1Y according to the third embodiment.

Figure 11:
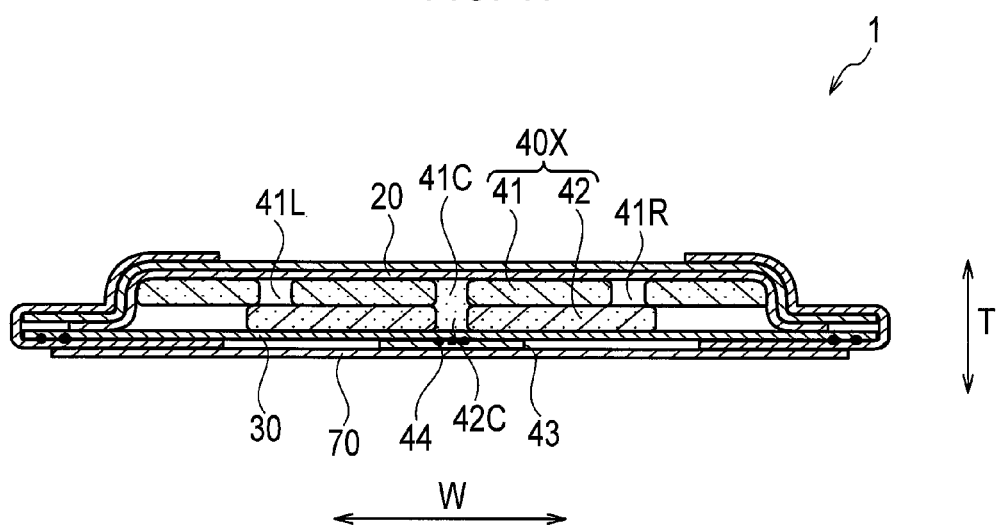
FIG. 11 is a widthwise sectional view of the disposable diaper 1Y according to the third embodiment (the line A-A of FIG. 10 as the reference).

FIG. 11 is a sectional view of the disposable diaper 1Y (the line A-A of FIG. 10 as the reference).

Figure 12:
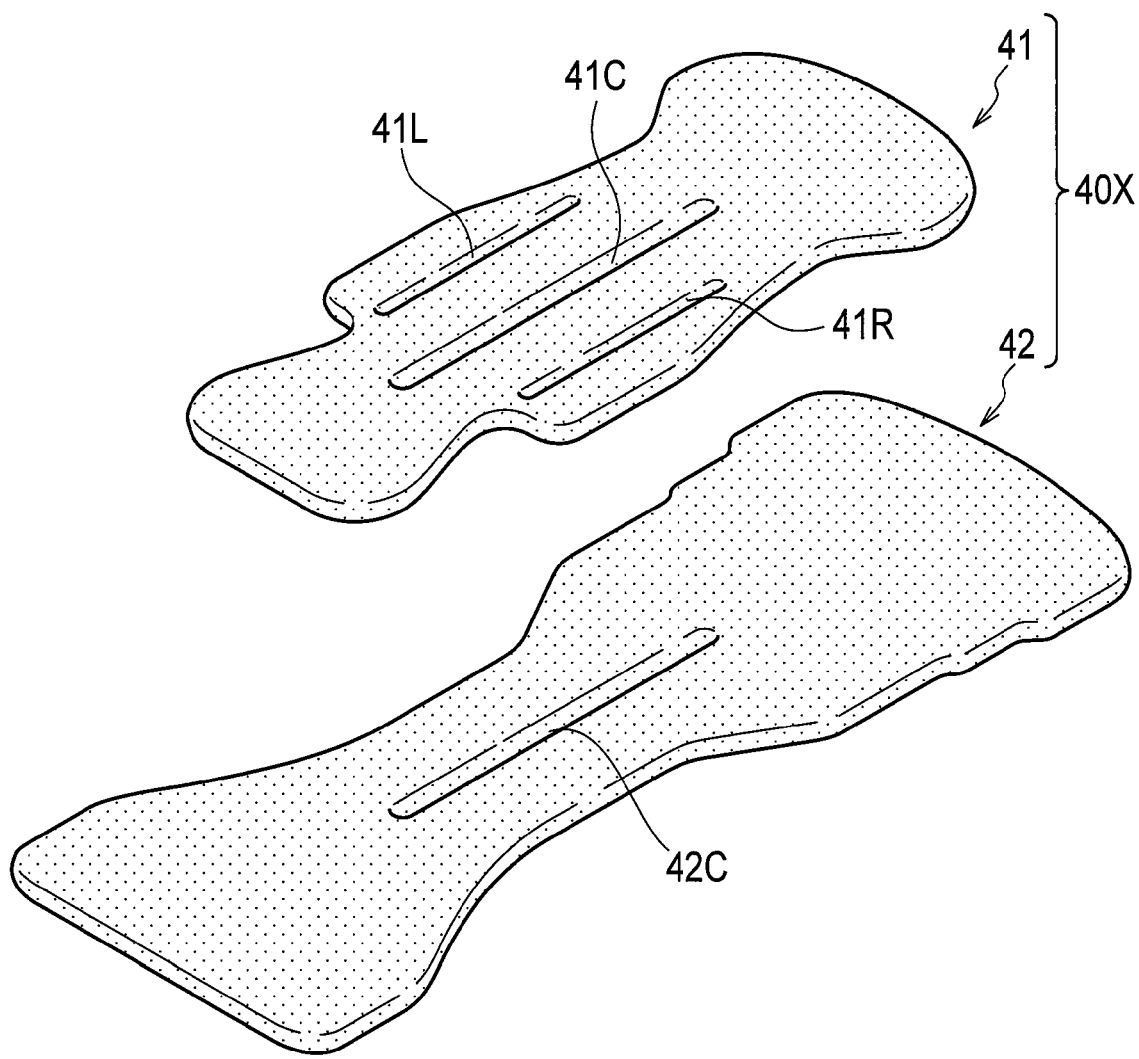
FIG. 12 is a perspective view of an absorber 40X according to the third embodiment.

FIG. 12 is a perspective view of an absorber 40X according to the third embodiment. As illustrated in FIG. 10 to FIG. 12, the absorber 40X according to the present embodiment has a two layer structure.

Specifically, the absorber 40X has a first layer 41, and a second layer 42 overlapping the first layer 41.

The first layer 41 is positioned at the skin contact surface side with a wearer and the second layer 42 is positioned at the non-skin contact surface of the wearer.

The first layer 41 is formed with a central slit 41C extending along the lengthwise direction L, and side slits 41L and 41R extending along the lengthwise direction L.

The side slits 41L and 41R are formed in the crotch region S1, similarly to the side slits 46L and 46R.

The second layer 42 is formed with a central slit 42C extending along the lengthwise direction L.

The central slit 42C is formed in the crotch region S1, similarly to the central slit 45 or the like.

The first layer 41 is provided with a pair of constricted portions 41S constricted toward the center of the absorber 40X in the widthwise direction W.

Furthermore, the second layer 42 has a pair of overhang portions 42P overlapping the position of the constricted portions 41S and overhung toward the outside of the widthwise direction W.

In addition, the second layer 42 may also be positioned at the skin contact surface side with the wearer, and the first layer 41 may also be positioned at the non-skin contact surface side of the wearer.

The crossing elastic member 7A crosses the absorber 40X in the pair of constricted portions 41S.

Thus, the overhang portions 42P are contracted by the crossing elastic member 7A toward the center of the absorber 40X in the widthwise direction W.

The overhang portions 42P are easily contracted because they are formed only with the second layer 42.

Furthermore, in the present embodiment, the crossing elastic member 7A crosses the absorber 40X at the position of not crossing either of the central slit 41C (a central curved portion), and the side slits 41L and 41R (side curved portions).

Since no slits are formed in the backside middle crotch region S5 outside of the crossing elastic member 7A, the absorber 40X is difficult to be bent and is easy to be flat.

Furthermore, among the front waistline region S2 (the foreside middle crotch region S4) and the back waistline region S3 (the backside middle crotch region S5), at least a portion provided with the fit elastic bodies 9A of the back waistline region S3 (the backside middle crotch region S5) crosses the absorber 40X without being fixed to the absorber 40X (specifically, the absorber body 50).

That is, at the portion provided with the fit elastic bodies 9A, the absorber backside covering sheet 30 configuring the absorber body 50 is not joined with the exterior topsheet 70, and the fit elastic bodies 9A is joined with the exterior topsheet 70 and the backside exterior backsheet 80R.

That is, among the crossing elastic member 7A and the fit elastic bodies 9A, which cross the absorber 40X, only the crossing elastic member 7A is fixed to the absorber 40X.

According to the disposable diaper 1Y, in at least the back waistline region S3 (the backside middle crotch region S5), since only the crossing elastic member 7A is fixed to the absorber 40X between the crossing elastic member 7A and the fit elastic bodies 9A, which cross the absorber 40X, the absorber 40X contracted by the crossing elastic member 7A is not affected by the contraction of the fit elastic bodies 9A.

That is, the absorber 40X can be reliably contracted by the crossing elastic member 7A without being affected by the fit elastic bodies 9A.

In addition, the fit elastic bodies 9A are not always separated from the absorber 40X as described above. For example, the fit elastic bodies 9A in the front waistline region S2 (the foreside middle crotch region S4) may be fixed to the absorber 40X.

Furthermore, since the overhang portions 42P are formed at the constricted portions 41S as a single layer and are thinner than a two-layered portion, a portion of the constricted portions 41S, in which the absorber 40X is small, is supplemented, and the overhang portions 42P more easily rise by the side edges 50A.

[Other Embodiments]

As mentioned above, although the content of the present invention was disclosed through the embodiments of the present invention, the descriptions and drawings that form a part of this disclosure are not to be considered as limitation to the present invention.

From this disclosure, various alternate embodiments, examples, and operation technology will become apparent to one skilled in the art.

For example, in the aforementioned first and second embodiments, the disposable diaper 1 has been described as a pant-type disposable diaper; however, the present invention is not limited thereto. For example, the present invention can also be applied to an open-type disposable diaper, a urine-absorbing pad or the like.

In the aforementioned embodiments, the central curved portion is formed using the slit or the elastic member. However, the central curved portion may also be formed by reducing the thickness of the absorber, or by embossing the absorber.

Furthermore, in the aforementioned embodiments, the absorber provided with the constricted portions and having a complicated plane shape has been used. However, a rectangular absorber may also be used.

As described above, needless to say, the present invention includes various embodiments and the like not described here.

Therefore, the technical range of the present invention is to be defined only by the inventive specific matter according to the adequate claims from the above description.

The entire contents of Japanese Patent Application Laid-open No. 2010-043595 (filed on Feb. 27, 2010) are incorporated in the present description by reference.

[Industrial Applicability]

As described above, according to the present invention, it is possible to provide a disposable worn article, such as a pant-type diaper, capable of surely striving for the comfort of a wearer when wearing the disposable worn article and preventing leakage of bodily waste by curving an absorber, and further improving absorbing power

[Description of the Numerals]

1, 1X, 1Y . . . disposable diaper, 3 . . . waist gather, 3A . . . waist elastic member, 4, 4' . . . front waistline edge portion, 5 . . . leg gather, 5A, 5B . . . leg elastic member, 6, 6' . . . back waistline edge portion, 7 . . . absorber crossing gather, 7A . . . crossing elastic member, 8 . . . middle crotch edge portion, 9A . . . fit elastic body, 10 . . . topsheet, 20 . . . absorber topside covering sheet, 30 . . . absorber backside covering sheet, 40, 40X . . . absorber, 40e . . . outside side end, 41 . . . first layer, 41C . . . central slit, 41L, 41R . . . side slit, 41S . . . constricted portion, 42 . . . second layer, 42C . . . central slit, 42P . . . overhang portion, 45 . . . central slit, 45a . . . apex surface, 46L, 46R . . . side slit, 47 . . . concave portion, 48 . . . rear portion, 50 . . . absorber body, 50A . . . side edge, 60 . . . sidesheet, 70 . . . exterior topsheet, 80F . . . foreside exterior backsheet, 80R . . . backside exterior backsheet, 90 . . . side elastic member, 110, 120, 130 . . . joining portion, 121, 123 . . . wide portion, 122 . . . narrow portion, S1 . . . crotch region, S2 . . . front waistline region, H1 . . . waistline opening, H2 . . . leg-hole opening, S3 . . . back waistline region, S4 . . . foreside middle crotch region, S5 . . . backside middle crotch region

The invention claimed is:

1. A disposable article, comprising:
   a front waistline region;
   a back waistline region;
   a crotch region positioned between the front waistline region and the back waistline region, and configured to be brought into contact with a crotch portion of a wearer;
   a pair of middle crotch regions positioned between the crotch region and the front waistline region and between the crotch region and the back waistline region,
   an absorber having a lengthwise direction, a widthwise direction perpendicular to the lengthwise direction, an inward direction toward the wearer, and an outward direction opposite to the inward direction;
   a central curved portion formed in the absorber along the lengthwise direction such that the absorber is curved to be convex toward the inward direction in the crotch region;
   a pair of side curved portions formed in the absorber along the lengthwise direction such that the absorber is curved to be convex toward the outward direction at outside of the widthwise direction from the central curved portion; and
   a crossing elastic member crossing the absorber along the widthwise direction in at least either of the pair of middle crotch regions, and fixed to the absorber,
   side elastic members provided at both ends of the absorber along the lengthwise direction,
   wherein
   an apex surface of the absorber being convex by the central curved portion toward the inward direction is configured to make contact with the crotch portion,
   the absorber is contracted by the crossing elastic member toward a center of the absorber in the widthwise direction,
   a width in which the crossing elastic member is fixed to the absorber is narrower than a width of the absorber in the middle crotch region, and
   a portion in which the crossing elastic member is not fixed is formed at the both ends of the absorber.

2. The disposable article according to claim 1, wherein the absorber is formed with a concave portion concaved by the crossing elastic member toward the center of the absorber in the widthwise direction.

3. The disposable article according to claim 1, wherein the crossing elastic member is provided at a non-skin contact surface side of the absorber.

4. The disposable article according to claim 1, wherein the width of the absorber in a portion in which the crossing elastic member is positioned is equal to or more than a width of the crotch region.

5. The disposable article according to claim 1, wherein the crossing elastic member is provided in the middle crotch region formed between the crotch region and the back waistline region.

6. The disposable article according to claim 1, wherein a waistline elastic member is provided in at least either of the front waistline region or the back waistline region to extend along the widthwise direction and to cross the absorber without being fixed to the absorber.

7. The disposable article according to claim 6, wherein the disposable article is a pants-type disposable article formed with a waistline opening and a pair of leg-hole openings, and
only the crossing elastic member crossing the absorber, among the crossing elastic member and the waistline elastic member, is fixed to the absorber.

8. The disposable article according to claim 1, wherein the crossing elastic member extends to the front waistline region or the back waistline region.

9. The disposable article according to claim 1, wherein the absorber comprises:
   a first layer; and
   a second layer overlapping the first layer.

10. The disposable article according to claim 9, wherein the first layer is provided with a pair of constricted portions constricted toward the center of the absorber in the widthwise direction; and
the crossing elastic member crosses the absorber in the pair of constricted portions.

11. The disposable article according to claim 10, wherein the second layer has a pair of overhang portions overlapping a position of the constricted portions and overhung toward an outside of the widthwise direction; and
the overhang portions are contracted by the crossing elastic member toward the center of the absorber in the widthwise direction.

12. The disposable article according to claim 1, wherein the central curved portion is formed with a central slit formed in the absorber along the lengthwise direction, or a central elastic member arranged along the lengthwise direction.

13. The disposable article according to claim 1, wherein the crossing elastic member crosses the absorber at the position of not crossing either of the central curved portion and the pair of side curved portions.

14. The disposable article according to claim 1, wherein the crossing elastic member crosses only the central curved portion among the central curved portion and the pair of side curved portions.

* * * * *